United States Patent [19]

Valducci

[11] Patent Number: 4,957,746
[45] Date of Patent: Sep. 18, 1990

[54] PROCESS FOR PREPARING ETOFIBRATE OR SIMILAR COMPOUNDS CONTAINING SUSTAINED RELEASE MICROGRANULES AND PRODUCTS THUS OBTAINED

[76] Inventor: Roberto Valducci, Via del Sole, 4, Savignano Sul Rubicone, Italy, 47039

[21] Appl. No.: 247,914

[22] Filed: Sep. 22, 1988

Related U.S. Application Data

[63] Continuation of Ser. No. 746,969, Jun. 20, 1985, abandoned.

[30] Foreign Application Priority Data

Jun. 29, 1984 [IT] Italy ............................ 3511 A/84

[51] Int. Cl.$^5$ .............................................. A61K 9/16
[52] U.S. Cl. .................................... 424/490; 424/487; 424/496; 424/497
[58] Field of Search ............... 424/490, 487, 496, 497

[56] References Cited

U.S. PATENT DOCUMENTS

| | | | |
|---|---|---|---|
| 4,000,254 | 12/1976 | Gordon et al. | 424/497 |
| 4,064,230 | 12/1977 | Gordon et al. | 424/461 |
| 4,515,804 | 5/1985 | Marti et al. | 514/894 |

Primary Examiner—Merrell C. Cashion, Jr.
Assistant Examiner—P. L. Prater
Attorney, Agent, or Firm—Darby & Darby

[57] ABSTRACT

The present invention relates to the pharmaceutical field and particularly to the manufacturing of a pharmaceutical product named etofibrate in the form of sustained release microgranules, wherein each microgranule consists entirely of an etofibrate composition and polyethylene glycol 4000, said microgranules being placed in capsules that, size of known capsules being equal, display an higher concentration of the active ingredient, the process for preparing the above microgranules comprising mainly the manufacturing of a compound consisting of etofibrate and solvent, wherein said compound is obtained in rotatory pan, then submitting this compound to a first sieving, placing it again in rotatory pan, drying the product thus obtained and sieving it once more, separating the microgranules which are replaced in the rotatory pan and then coated in rotatory pan with further etofibrate added with a suitable amount of polyethylene glycol 4000 to give, after a last sieving, the desired microgranules whose size corresponds to the requested size and is normally comprised between 400 and 2000 microns.

18 Claims, No Drawings

PROCESS FOR PREPARING ETOFIBRATE OR SIMILAR COMPOUNDS CONTAINING SUSTAINED RELEASE MICROGRANULES AND PRODUCTS THUS OBTAINED

This is a continuation of application Ser. No. 746,969, filed Jun. 20, 1985, now abandoned.

BACKGROUND OF THE INVENTION

1. Field of the Invention

The present invention relates to a new composition of etofibrate microgranules which are differently formulated and differently manufactured in comparison to the already available product.

2. Description of the Prior Art

Etofibrate is in fact a known compound having the following pharmacological properties: it reduces hyperlipidemia, hypertriglyceridemia and hypercholesterolemia.

Said etofibrate is a compound corresponding to the chemical name 2-(p-chlorophenoxy)-2-methylpropionic acid [2-(nicotinoyloxy)-ethyl]-ester. This product is on the market since many years and is available in form of hard "00" type gelatine capsules containing 500 mg of etofibrate as sustained release microgranules. These capsules, with a capacity of 0.95 ml, are able to contain the above microgranules which are composed of an inert material inner core coated with a spheroidal layer of active ingredient comprising etofibrate and polyethylene glycol 4000, also known on the market as polyglycol 4000. This result, that has been achieved by means of particular per se known processes, entails each microgranule to have a concentration ranging from 67 to 75% of active ingredient, as even each microgranule consists also of an inert material inner core with a diameter of 850–500 microns comprising from 65 to 90% of sucrose and from 10 to 35% of corn starch. The presence in each microgranule of an inner core binds evidently to use the above "00" type of capsules, being only these capsules able to contain the mentioned dosage of 500 mg per capsule.

OBJECTS

Aim of the present invention was to obtain an higher concentration of etofibrate, so that the 500 mg standard dosage might be placed in smaller gelatine capsules. In each capsule an higher dosage of 750 mg of active ingredient may also be included.

It is therefore possible to have the 500 mg standard dosage placed not in the "00" type capsules but rather in a "0" type capsule (0.68 ml), thus evidently facilitating its deglutition.

Because of components percentage and of its particular constitution, this composition allows a sustained release of the drug and eliminates the well-known flash, characteristic side-effect of etofibrate.

Further aim of the present invention was to prepare spherical microgranules by means of simple procedures, said microgranules having a diameter ranging from 400 to 2000 microns and an etofibrate concentration of 88-98%, in other words spherical microgranules without inert core and, therefore, with an higher concentration of active ingredient.

SUMMARY OF THE INVENTION

These and other aims have been achieved with the present invention, characterized in that the provided process comprises the following manufacturing features:

preparation in rotatory pan of a compound consisting of etofibrate and solvent, said compound being then submitted to a first sieving and replaced in rotatory pan, the product being subsequently dried and resieved, the microgranules being separated and then introduced in rotatory pan, wherein the microgranules thus obtained are coated with further etofibrate added with a suitable percentage of polyethylene glycol 4000 to give, after a last sieving, the ultimate microgranules having a size corresponding to the requested size and which is normally comprised between 400 and 2000 microns.

The product obtained with the above process consists at contrary of a "0" type (0.68 ml), or "0" extended type (0.80 ml) or of a "00" type capsule (0.95 ml) containing respectively 500, 600 or 750 mg of active ingredient, wherein said active ingredient consists of several microgranules having a diameter between 400 and 2000 microns, each microgranule comprising an etofibrate inner core and an outer coat of etofibrate added with polyethylene glycol 4000, wherein the total percentage of etofibrate is comprised between 89 and 98%, whereas the total percentage of polyethylene glycol 4000 ranges from 11 and 2% respectively.

From what stated above, it may be clearly argued that, in comparison to the prior art, each capsule is filled with many microgranules, all being lacking in inert core and, therefore, at high concentration of active ingredient, and having particular percentages of the active ingredient compositions which confer the mentioned advantages.

Further features and advantages of the invention will be made clear in the following detailed description that is given only for illustrative but not limitative purposes.

DESCRIPTION OF THE PREFERRED EMBODIMENT

The process used to obtain the product of the present invention provides the following procedures, each being only given as exemplificatory.

Generally, the process comprises the following steps:

(a) powdered etofibrate (or a substance having similar properties) was placed in a rotating pan, then solvent was added and the mixture was worked in the same pan;

(b) the compound was submitted to a first sieving and the first microgranules thus obtained were reworked in the pan that was being rotated for a while;

(c) the product comprising these first microgranules was dried until the solvent was evaporated off, then it was sieved again thus separating other microgranules or cores having a pre-determined diameter, which however is lower than the diameter of the first microgranules;

(d) said second microgranules or cores were replaced in the rotating pan and, by means of suitable pumps or by spraying, they were coated with further etofibrate to which a suitable amount of polyethylene glycol 4000 has been added;

(e) a last sieving was carried out to separate only these third microgranules, whose size corresponds to the required size and is comprised between 400 and 2000 microns;

(f) said third microgranules were then placed in suitable capsules.

A detailed example of the process described above is reported here below.

Referring to an amount of 50 kg of etofibrate, this powder was placed in a pan having a steel basket rotating at 10–20 rpm; 10 kg of acetone were added and the pan was being rotated for 10–25 minutes.

The product was discharged and placed in a net granulator of 14–20 mesh. The granulate thus obtained (or first microgranules) was replaced in the pan, rotating for 10/25 minutes. The product was dried for 10/20 minutes at 30° C. in a thermostatic drier, i.e. until all the acetone was evaporated off.

The dried granulate was then resieved, thus selecting the fraction comprised between 300 and 1000 microns and consisting of the second microgranules or cores.

Said fraction was placed in the rotating pan and by spraying with high pressure pumps the cores were coated with previously fused etofibrate to which polyethylene glycol 4000 was added. As to the sprayed etofibrate, the amount of polyethylene glycol 4000 is comprised between 3 and 12%. These (third) microgranules thus obtained were sieved for a last time and they were showing a diameter comprised between 400 and 2000 microns.

A further procedure could be fully identical to the procedure described above, with the sole exception that the etofibrate applied on the previously formed cores was not melted in advance.

For coating these nuclei with etofibrate, the product was brought into solution with a solvent (acetone) by preparing a cold saturated solution or, if a lower concentration is desired, the solution etofibrate-acetone was heated between 35° and 45° C. In both cases, to the etofibrate solution the 3–12% of polyethylene glycol 4000, based on the etofibrate, was added. The microgranules obtained with the procedures and methods described above were then placed into capsules that are well known in the art as hard gelatine capsules and that can be of several sizes, that is of "0" type, containing 0.68 ml, or of extended "0" (0.80 ml) or of "00" type (0.95 ml).

The product obtained with the above process consists therefore of one of said capsules containing respectively 500, 600 or 750 mg of active ingredient. Said active ingredient comprises all the (third) microgranules having a diameter ranging from 400 to 2000 microns. Each of these microgranules consists therefore of an etofibrate inner core and of an outer layer of etofibrate added with polyethylene glycol 4000, according to the above process, the whole having amounts of etofibrate ranging from 89 and 98% and amounts of polyethylene glycol 4000 comprised between 11 and 2% respectively. Evidently each microgranule consists mainly and entirely of active ingredient, owing to the fact it comprises an inner core of etofibrate alone. Logically each microgranule consists entirely of active ingredient with a very high amount of etofibrate, and therefore all the microgranules corresponding to a standard dosage of pharmaceutical product will take up less room and less volume, so that on one hand the therapeutic activity of the capsules can be increased, size of known capsules being equal, and on the other hand their size may be decreased, amount of active ingredient being equal.

What is claimed is:

1. A process for preparing encapsulated sustained release etofibrate formulations comprising:
   (a) mixing powdered etofibrate with a solvent, working said etofibrate and said solvent in a rotating pan;
   (b) sieving the contents of said rotating pan from step (a) to recover a first product comprising first microgranules;
   (c) returning said first product to said rotating pan and reworking said first product in said rotating pan;
   (d) removing the solvent from and drying the contents of said rotating pan from step (c);
   (e) sieving the dried contents of said rotating pan from step (d) to recover a second product comprising second microgranules, said second microgranules having diameters smaller than those of said first microgranules;
   (f) placing said second product in said rotating pan and coating said second product with a mixture of etofibrate and polyethylene glycol such that the total etofibrate content of the coated microgranules subsequently recovered in step (g) is within the range of 89–98% by weight based on the weight of said microgranules said total etofibrate content achieved through the serial addition of etofibrate with intermediate sieving and return of the sieved and return of the sieved material for additional coating with etofibrate;
   (g) sieving the contents of said rotating pan from step (f) to recover a third product comprising third microgranules, said third microgranules having diameters between 400 and 2000 microns; and
   (h) encapsulating said third microgranules.

2. A process as claimed in claim 1, wherein said pharmaceutically active compound is etofibrate.

3. A process as claimed in claim 2, wherein the amount of said solvent mixed with etofibrate in step (a) is 10 to 40% by weight, based on the weight of etofibrate.

4. A process as claimed in claim 1, wherein during said step (a), said rotating pan is rotated at a speed of about 10 to 20 revolutions per minute, for a time period of about 10 to 25 minutes.

5. A process as claimed in claim 4, wherein during said step (b), said sieving is carried out using a granulator having a mesh size of about 14 to 20 mesh.

6. A process as claimed in claim 5, wherein said reworking during said step (c) is carried out for a period of about 10 to 25 minutes.

7. A process as claimed in claim 6, wherein during said step (d), said first product is dried for about 10 to 20 hours at about 30° C.

8. A process as claimed in claim 5, wherein said second microgranules have a diameter of about between 300 and 1,000 microns.

9. A process as claimed in claim 3, wherein during said step (f), said coating is carried out by spraying said second product with a pressurized mixture containing etofibrate and 3–12% by weight polyethylene glycol, based on the weight of etofibrate in said mixture.

10. A process as claimed in claim 9, further comprising obtaining said mixture containing etofibrate and polyethylene glycol by mixing a solution of etofibrate in a solvent, with polyethylene glycol in the amount of 3–12% by weight, based on the weight of etofibrate in said solution.

11. A process as claimed in claim 10, wherein said solvent is acetone.

12. An encapsulated sustained release etofibrate formulation comprising microgranules, each of which has a diameter within the range of about 400 to about 2000 microns and comprises an inner core of etofibrate and an outer layer of etofibrate and polyethylene glycol said core of etofibrate added through the serial addition of etofibrate with intermediate sieving and return of the sieved material for additional coating with etofibrate, wherein:

the amount of etofibrate in each of said microgranules added through serial addition with intermediate sieving is within the range of about 89-98% by weight, and the amount of polyethylene glycol in each of said microgranules is within the range of about 2-11% by weight based on the weight of the microgranules;

the total etofibrate content in said formulation is about 500 mg.

13. An encapsulated sustained release etofibrate formulation comprising microgranules, each of which has a diameter within the range of about 400 to 2000 microns and comprises an inner core of etofibrate and an outer layer of etofibrate and polyethylene glycol said core of etofibrate added through the serial addition of etofibrate with intermediate sieving and return of the sieved material for additional coating with etofibrate, wherein:

the amount of etofibrate in each of said microgranules is within the range of about 89-98% by weight and the amount of polyethylene glycol in each of said microgranules is about 2-11% by weight, based on the weight of the microgranules;

the total volume of said formulation is 0.80 ml; and the total etofibrate content in said formulation is about 600 mg.

14. An encapsulated sustained release etofibrate formulation comprising microgranules, each of which has a diameter within the range of about 400 to 2000 microns and comprises an inner core of etofibrate and an outer layer of etofibrate and polyethylene glycol said core of etofibrate added through the serial addition of etofibrate with intermediate sieving and return of the sieved material for additional coating with etofibrate, wherein:

the total volume of said formulation is 0.95 ml; and the total etofibrate content in said formulation is about 750 mg.

15. An encapsulated sustained release etofibrate formulation comprising microgranules, each of which has a diameter within the range of about 400 to 2000 microns and comprises an inner core of etofibrate and an outer layer of etofibrate and polyethylene glycol, wherein:

the amount of etofibrate in each of said microgranules is within the range of about 89-98% by weight and the amount of polyethylene glycol in each of said microgranules is about 2-11% by weight, based on the weight of said microgranules;

the total volume of said formulation is 0.95 ml; and the total etofibrate content in said formulation is about 750 mg.

16. An encapsulated sustained release formulation comprising microgranules, each of which has a diameter within the range of about 400 to about 2000 microns and comprises an inner core of a pharmaceutically active compound and an outer layer of a coating material suitable for obtaining a sustained release product, and wherein:

the total volume of said formulation is 0.68 ml; and the total content of said pharmaceutically active compound in said formulation is about 500 mg.

17. An encapsulated sustained release formulation comprising microgranules, each of which has a diameter within the range of about 400 to about 2000 microns and comprises an inner core of a pharmaceutically active compound and an outer layer of a coating material suitable for obtaining a sustained release product, and wherein:

the total volume of said formulation is 0.80 ml; and the total content of said pharmaceutically active compound in said formulation is about 600 mg.

18. An encapsulated sustained release formulation comprising microgranules, each of which has a diameter within the range of about 400 to about 2000 microns and comprises an inner core of a pharmaceutically active compound and an outer layer of a coating material suitable for obtaining a sustained release product, and wherein:

the total volume of said formulation is 0.95 ml; and the total content of said pharmaceutically active compound in said formulation is about 750 mg.

* * * * *